(12) United States Patent
Peng et al.

(10) Patent No.: US 8,298,766 B2
(45) Date of Patent: Oct. 30, 2012

(54) FLUORESCENT DYES, METHODS OF SYNTHESIS AND APPLICATIONS THEREOF

(76) Inventors: Xiaojun Peng, Dalian (CN); Tong Wu, Dalian (CN); Jiangli Fan, Dalian (CN); Shiguo Sun, Dalian (CN)

( * ) Notice: Subject to any disclaimer, the term of this patent is extended or adjusted under 35 U.S.C. 154(b) by 0 days.

(21) Appl. No.: 13/119,752

(22) PCT Filed: Apr. 30, 2010

(86) PCT No.: PCT/CN2010/072378
§ 371 (c)(1),
(2), (4) Date: Mar. 18, 2011

(87) PCT Pub. No.: WO2011/082566
PCT Pub. Date: Jul. 14, 2011

(65) Prior Publication Data
US 2011/0262904 A1    Oct. 27, 2011

(30) Foreign Application Priority Data

Jan. 5, 2010 (CN) .......................... 2010 1 0022414

(51) Int. Cl.
*C12Q 1/68* (2006.01)
*C07D 413/14* (2006.01)
*C07D 417/06* (2006.01)
*C07D 421/06* (2006.01)

(52) U.S. Cl. ......................................... 435/6.1; 546/165

(58) Field of Classification Search ........................ None
See application file for complete search history.

(56) References Cited

U.S. PATENT DOCUMENTS

| 5,658,735 A * | 8/1997 | Lee .............................. 435/6.12 |
| 2009/0017441 A1 * | 1/2009 | Peng et al. ........................ 435/4 |
| 2009/0176270 A1 * | 7/2009 | Shao ............................ 435/40.5 |

OTHER PUBLICATIONS

Richard B. Silverman, The Organic Chemistry of Drug Design and Drug Action: Chapter 2: Drug Discovery, Design and Development, Academic Press (1992).*
Kerns & Di, Drug-like Properties: Concepts, Structure Design & Methods: from ADME to Toxicity Optimization, Academic Press, pp. 92-93 (2008).*

* cited by examiner

*Primary Examiner* — Janet Andres
*Assistant Examiner* — Timothy R Rozof
(74) *Attorney, Agent, or Firm* — Allen (Zhi Yang) Xue; Anova Law Group, PLLC (57) ABSTRACT

The present invention provides a category of cyanine dyes having the following general structural Formula I, wherein X is defined as $C(CH_3)_2$, O, S or Se; m is an integer from 1 to 18, $R_1$ and $R_2$ are each independently chosen from H, $C_{1-18}$alkyl, $OR_7$, $C_{1-6}$alkyl-$OR_7$ or halogen; $R_3$ is pyrrolyl, imidazolyl, piperidinyl, piperazinyl, morpholinyl, guanidino, $NHR_5$ or $N(R_6)_2$; $R_4$ is $C_{1-18}$alkyl, benzyl or $(CH_2)_mR_3$; $R_5$ is saturated and/or unsaturated, straight-chained and/or branched-chained $C_{1-18}$alkyl, hydroxy alkyl, mercapto-alkyl, amino alkyl, acyl, phenyl, naphthyl or benzyl; $R_6$ is a $C_{2-18}$alkyl; $R_7$ is H or a $C_{1-18}$alkyl; $Y^-$ is an anion. The mentioned compounds can be applied to staining biological samples, to the fields of nucleic acids labeling, blood cell analysis, clinical diagnosis, immunological assays and etc.

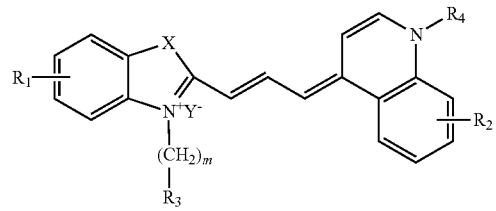

13 Claims, 5 Drawing Sheets

FLUORESCENT DYES, METHODS OF SYNTHESIS AND APPLICATIONS THEREOF

CROSS-REFERENCES TO RELATED APPLICATIONS

The present application claims the benefit of the Chinese Patent Application No. 201010022414.6, filed Jan. 5, 2010, which is incorporated herein by reference in its entirety and for all purposes.

FIELD OF THE INVENTION

The present invention relates to a novel category of fluorescent dyes, their synthesizing methods and applications in fine chemical domains, particularly a category of monocationic nitrogen containing cyanine dyes, their synthesizing methods and application utilizing the mentioned cyanine dyes, their conjugates or compositions for biological staining.

BACKGROUND OF THE INVENTION

Fluorescent dyes as functional molecules have been widely used in various fields of science and technology. Studies on them in life science, clinical diagnosis, immunological assays and etc become the focus of attention throughout the whole world. At present, phenanthridines (EB, PI), acridines (AO), imidazoles (Hoechst, DAPI), cyanine dyes (Cy, TOTO, SYTO) and other commercially available fluorescent dyes have played significant role in the fields of genomics, quantitative detection of nucleic acids, blood cell analysis and etc. However, all these commercially available fluorescent dyes have their own application limitations. The major problem is many of them are restricted to fixed cell samples, such as TOPRO, the TOTO dye family, ethidium bromide (EB), and propidium iodide (PI), which require membrane permeabilization or similar method to label the DNA efficiently. However, fixation of cells often produces undesired artifacts [S. Kozubek, E. Lukasova, J. Amrichova, M. Kozubek, A. Liskova, J. Slotova, *Anal. Biochem.* 2000, 282, 29-38]. At the same time, acridine and phenanthridine dyes such as EB are toxic and carcinogenic. Secondly, there are a considerable number of fluorescent dyes need ultraviolet illumination as excitation light source, such as DNA specific crescent-shaped dyes 4',6-diamidino-2-phenylindole (DAPI), Hoechst33258, Hoechst34580, which emit blue fluorescence upon binding to DNA. As the UV light damages cellular DNA, protein and other components, the use of them is very restricted in time [S. K. Davis, C. J. Bardeen, *Photochem. Photobiol.* 2003, 77, 675-679]. Besides, it's difficult for excitation light to penetrate into the inside biological tissues due to the strong absorption of ultraviolet light by some components in biological samples. Furthermore, the self fluorescence of some biological components may lead to a high fluorescence background that interferes with detection. Therefore, exploring novel fluorescent dyes meeting the multiple criteria of excellent spectral properties, low toxicity and live cell permeability is still the key to promote the development of fluorescent analysis technology, life science and other fields.

Among various sorts of fluorescent dyes, cyanine dyes with their wide wavelength emission scope, large molar extinction coefficient and proper fluorescence quantum yield, are extensively applied as biofluorescent probes, CD or VCD recording materials, photosensitive agents for photosensitive materials, photoelectric conversion materials, etc. Quinoline asymmetric cyanine dyes stand out from all cyanine classes in the applications of areas such as genomics, nucleic acids quantitative detection, blood cell analysis and etc because of their specificity showing high affinity with nucleic acids and basically no association with other biomacromolecules. The interaction modes of these asymmetric cyanine dyes with nucleic acids are intercalation to base pairs, groove binding and electrostatic attraction. Specific binding mode and binding affinity depends on the structure of the dyes and the ratio of dyes to base pairs. A typical type of asymmetric cyanine dyes are TOTO and its analogues and derivatives thereof. TOTO (thiazole orange dimer) and YOYO (oxazole orange dimer), developed by Glazer research group, are multicationic asymmetric cyanine fluorescent dyes having a high affinity to nucleic acids, of which different heterodimeric analogues and derivatives can be obtained by changing the dye molecules on the ends of the polymethine bridge. These dyes show no fluorescence in solution, which reduces the interference from the fluorescence background during detection, but do upon binding to nucleic acids. Jason et al explored the double intercalation of TOTO and YOYO into DNA using solution viscosity measurements and atomic force microscopy [J. A. Bordelon, K. J. Feierabend, S. A. Siddiqui, L. L. Wright, J. T. Petty, *J. Phys. Chem. B* 2002, 106, 4838-4843]. Fürstenberg et al further expounded the dynamic mechanism of the fluorescence enhancement using ultrafast fluorescence up-conversion and time-correlated single photon counting technology [A. Fürstenberg, M. D. Julliard, T. G. Deligeorgiec, N. I. Gadjev, *J. Am. Chem. Soc.* 2006, 128, 7661-7669]. Many of this type of asymmetric cyanine dyes are commercially available, such as SYTOX, TOTO, POPO, BOBO, YO-PRO and etc. But such commercially available dyes usually have large molecular weight and complex structures, which are live cell impermeant and can only be utilized to nucleic acids detection in vitro.

BRIEF SUMMARY OF THE INVENTION

So currently it is still in great demand of novel fluorescent dyes with the following characteristics: showing low fluorescence background in the absence of nucleic acids, high quantum yield upon binding to nucleic acids and no affinity for biomolecules except for nucleic acids; having a certain level of water solubility, as well as good live cell permeability; exhibiting spectral range with obvious discrepancy from that of biological samples.

In one aspect, against the inadequacies in existing technologies, the present invention provides a novel category of compounds with simple structure, high sensitivity, long wavelength and live cell permeability, which include compounds of Formula I as follow:

wherein X is $C(CH_3)_2$, O, S or Se m is an integer from 1 to 18.

$R_1$ and $R_2$ are each independently selected from the group consisting of H, $C_{1-18}$alkyl, $OR_7$, $C_{1-6}$alkyl-$OR_7$ and halogen.

$R_3$ is selected from the group consisting of pyrrolyl, imidazolyl, piperidinyl, piperazinyl, morpholinyl, guanidino, $NHR_5$ and $N(R_6)_2$.

$R_4$ is selected from the group consisting of $C_{1-18}$alkyl, benzyl and $(CH_2)_mR_3$; Said benzyl is optionally substituted with one or more substituents, independently selected from the group consisting of H, $C_{1-18}$alkyl, CN, COOH, $NH_2$, $NO_2$, OH, SH, $C_{1-6}$alkoxy, $C_{1-6}$alkyl amino, $C_{1-6}$amido, halogen and $C_{1-6}$ halo-alkyl.

$R_5$ is selected from the group consisting of saturated and/or unsaturated, straight-chained and/or branched-chained $C_{1-18}$alkyl, hydroxy alkyl, mercapto-alkyl, amino alkyl, acyl, phenyl, naphthyl and benzyl; Said phenyl, naphthyl or benzyl is optionally substituted with one or more substituents, independently selected from the group consisting of H, $C_{1-18}$alkyl, CN, COOH, $NH_2$, $NO_2$, OH, SH, $C_{1-6}$alkoxy, $C_{1-6}$alkyl amino, $C_{1-6}$amido, halogen and $C_{1-6}$ halo-alkyl

$R_6$ is a $C_{2-18}$alkyl $R_7$ is H or a $C_{1-18}$alkyl $Y^-$ is an anion.

In another aspect, the present invention further provides a method for synthesizing the above-mentioned compounds of Formula I which includes the following steps:

1) reacting 4-methyl-quinoline heterocyclic aromatic compound II with compound $R_4Z$ to obtain the first quaternary ammonium slat intermediate III, wherein Z is halogen or OTs and $Z^-$ is the reaction generated halogen anion or $OTs^-$:

wherein a reaction temperature is 10-180° C., a reaction time is 4-48 h, a reaction solvent is dichloromethane, chloroform, ethanol, acetonitrile, ethyl acetate, toluene, xylene, o-dichlorobenzene or mixtures thereof, and a molar ratio of II to compound $R_4Z$ is 1:1-1:10;

2) condensing the first quaternary ammonium slat intermediate III from 1) with N,N'-diphenylformamidine to get the compound of Formula IV:

wherein a reaction temperature is 50-200° C., and a reaction time is 15 min-4 h, and the reaction is solvent-free or carried out in a solvent of acetic anhydride, acetic acid or mixture thereof, and the molar ratio of the first quaternary ammonium slat intermediate III to N,N'-diphenylformamidine is 1:1-1:4;

3) reacting compound V with compound $R_3(CH_2)_mZ$ to obtain the second quaternary ammonium slat intermediate VI, wherein Z is halogen or OTs and $Z^-$ is the reaction generated halogen anion or $OTs^-$:

wherein a reaction temperature is 10-180° C., and a reaction time is 4-48 h, a reaction solvent is dichloromethane, chloroform, ethanol, acetonitrile, ethyl acetate, toluene, xylene, o-dichlorobenzene or mixtures thereof, and a molar ratio of V to compound $R_3(CH_2)_mZ$ is 1:1-1:10;

4) reacting the second quaternary ammonium slat intermediate VI from 3) with IV to give the compound of Formula VII:

wherein a reaction temperature is 5-130° C., and a reaction time is 10 min-6 h, a reaction is solvent-free or carried out in a solvent of dichloromethane, chloroform, methanol, ethanol, ethylene glycol monomethyl ether or mixtures thereof. The catalyst for this reaction is a combination of acetic anhydride and organic base, and a molar ratio of VI to IV is 1.5:1-1:1.5 wherein X, m, $R_1$, $R_2$, $R_3$, $R_4$, $R_5$, $R_6$ and $R_7$ are defined according to claim 1.

5) replacing the anion of compound VII with $Y^-$ of the corresponding sodium or potassium to give the final compound of Formula I:

wherein a reaction temperature is 60-140° C., and a reaction time is 10 min-2 h, a reaction solvent is DMF, DMSO or mixtures thereof, and a molar ratio of sodium or potassium containing $Y^-$ to VII is 1:1-10:1;

wherein $Y^-$ is defined according to claim 1.

BRIEF DESCRIPTION OF THE DRAWINGS

FIG. 6A is the white light image of live MCF-7 cells (human breast cancer cells) stained with compound A, 6B is the fluorescence image of live MCF-7 cells stained with compound A. The concentration of compound A is 2 μM. The equipment used is a confocal laser scanning microscope (TCS-SP2). Excitation channel: Cy5 (633 nm).

FIG. 7A is the white light image of live MCF-7 cells (human breast cancer cells) stained with compound D, 7B is the fluorescence image of live MCF-7 cells stained with compound D. The concentration of compound D is 1.5 μM. The equipment used is a confocal laser scanning microscope (TCS-SP2). Excitation channel: Cy5 (633 nm).

FIG. 8A is the white light image of live MCF-7 cells (human breast cancer cells) stained with compound E, and 8B is the fluorescence image of live MCF-7 cells stained with compound E. The concentration of compound E is 3 μM. The equipment used is a confocal laser scanning microscope (TCS-SP2). Excitation channel: Cy5 (633 nm).

FIG. 9A is the white light image of live MCF-7 cells (human breast cancer cells) stained with compound $M_1$, 9B is the fluorescence image of live MCF-7 cells stained with compound $M_1$. The concentration of compound $M_1$ is 2 μM. The equipment used is a confocal laser scanning microscope (TCS-SP2). Excitation channel: Cy5 (633 nm).

DETAILED DESCRIPTION OF PREFERRED EMBODIMENTS

The following terms as used herein have the following definitions, unless otherwise stated.

The term "alkyl" as used herein includes straight and branched alkyl groups. In reference to a single alkyl such as "propyl" specifically means a straight alkyl group, while in reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The similar rules also apply to other groups as used throughout the present specification.

The term "halogen" as used herein includes fluorine, chlorine, bromine and iodine.

The term "benzyl" as used herein refers to —$CH_2$-phenyl group. Modification of a benzyl group with the phrase "optionally substituted with" means that the benzyl group either can exist in an unsubstituted form, or can be substituted with one or more suitable substituents at any suitable positions. Suitable substituents include, but are not limited to, H, $C_{1-18}$alkyl, CN, COOH, $NH_2$, $NO_2$, OH, SH, $C_{1-6}$alkoxy, $C_{1-6}$alkyl amino, $C_{1-6}$amido, halogen or $C_{1-6}$ halo-alkyl etc., so long as the compounds formed have the properties as contemplated by the present invention. Preferably, the benzyl group is optionally substituted with COOH, $NH_2$, OH, $C_{1-6}$alkoxy or halogen.

$Y^-$ as used herein stands for the counter ion and can be any suitable anion, which include, but not limited to inorganic or organic anions, e.g., halogen anions, $ClO_4^-$, $PF_6^-$, $BF_4^-$, $CH_3COO^-$ or $OTs^-$.

In preferred embodiments of the invention, compounds of Formula I are those in which X is $C(CH_3)_2$, O or S. In more preferred embodiments, X is $C(CH_3)_2$ or S and in the most preferred embodiment, X is S;

Preferred embodiments of the invention include compounds of Formula I wherein $R_1$ and $R_2$ are independently selected from the group consisting of H and $C_{1-18}$alkyl. More preferably, $R_1$ and $R_2$ are independently selected from the group consisting of H and $C_{1-12}$alkyl; even more preferably H or $C_{1-6}$alkyl. In the most preferred embodiment, $R_1$ and $R_2$ are both H.

Preferred embodiments of the invention also include compounds of Formula I wherein $R_3$ is selected from the group consisting of $NHR_5$, $N(R_6)_2$, pyrrolyl and piperidinyl. In the most preferred embodiment, $R_3$ is $NHR_5$ or $N(R_6)_2$.

Preferred embodiments of the invention also include compounds of Formula I wherein $R_4$ is selected from the group consisting of $C_{1-18}$alkyl and benzyl. More preferably, $R_4$ is selected from the group consisting of $C_{1-12}$alkyl and benzyl. In the most preferred embodiments, $R_4$ is selected from the group consisting of $C_{1-6}$ alkyl or benzyl. Said benzyl preferably optionally substituted with one or more substituents, independently selected from the group consisting of H, $C_{1-18}$alkyl, CN, COOH, $NH_2$, $NO_2$, OH, SH, $C_{1-6}$alkoxy, $C_{1-6}$alkyl amino, $C_{1-6}$amido, halogen and $C_{1-6}$ halo-alkyl; more preferably COON, $NH_2$, OH, $C_{1-6}$alkyl or halogen;

Preferred embodiments of the invention also include compounds of Formula I wherein $R_5$ is selected from the group consisting of saturated and/or unsaturated, straight-chained and/or branched-chained $C_{1-18}$alkyl and amino alkyl. In more preferred embodiments, $R_5$ is selected from the group consisting of saturated and/or unsaturated, straight-chained and/or branched-chained $C_{1-12}$alkyl. In the most preferred embodiments, $R_5$ is selected from the group consisting of saturated and/or unsaturated, straight-chained and/or branched-chained $C_{1-6}$alkyl.

Preferred embodiments of the invention include compounds of Formula I wherein $R_6$ is a $C_{2-6}$alkyl,

Preferred embodiments of the invention also include compounds of Formula I wherein $R_7$ is H or a $C_{1-6}$alkyl;

Preferred embodiments of the invention also include compounds of Formula I wherein $Y^-$ is a halogen anion, $ClO_4^-$, $PF_6^-$, $BF_4^-$, $CH_3COO^-$ or $OTs^-$;

In another aspect, the present disclosure further provides a method for synthesizing the above-mentioned compounds. The said method includes:

Prepare the first and second quaternary ammonium salt intermediate separately, next, the first or second intermediates are then condensed with N,N'-diphenylformamidine and finally reacted with the remaining ones to obtain the compounds of the present invention by the catalysis of acetic anhydride with organic base (such as amine). Specific synthesizing schemes are as follows:

First is the preparation of the first quaternary ammonium salt intermediate, which is the 4-methyl-quinoline heterocyclic aromatic compound II reacts with compound $R_4Z$ to obtain the first quaternary ammonium slat intermediate III, wherein Z is halogen or OTs, $Z^-$ is the halogen anion or $OTs^-$ generated in the reaction:

The reaction temperature is 10-180° C., and the reaction time is 4-48 h. The reaction solvent is dichloromethane, chloroform, ethanol, acetonitrile, ethyl acetate, toluene, xylene o-dichlorobenzene or the polar organic solvents of the mixture thereof. The molar ratio of II to compound $R_4Z$ is 1:1-1:10;

Preferably the reaction temperature is 40-140° C., and the reaction time is 6-36 h. The reaction solvent is chloroform, acetonitrile, toluene, xylene, o-dichlorobenzene or the polar organic solvents of the mixture thereof. The molar ratio of II to compound $R_4Z$ is 1:1-1:6;

More preferably the reaction temperature is 50-120° C., and the reaction time is 8-24 h. The reaction solvent is toluene, o-dichlorobenzene or the polar organic solvents of the mixture thereof. The molar ratio of II to compound $R_4Z$ is 1:1-1:3;

Most preferably the reaction temperature is 60-110° C., and the reaction time is 8-14 h. The reaction solvent is toluene, o-dichlorobenzene or the polar organic solvents of the mixture thereof. The molar ratio of II to compound $R_4Z$ is 1:1-1:1.5;

Secondly, condense the first quaternary ammonium slat intermediate III with N,N'-diphenylformamidine to get the compound of Formula IV:

The reaction temperature is 50-200° C., and the reaction time is 15 min-4 h. The reaction is solvent-free or carried out in a solvent of acetic anhydride, acetic acid or mixture thereof. The molar ratio of the first quaternary ammonium slat intermediate III to N,N'-diphenylformamidine is 1:1-1:4;

Preferably the reaction temperature is 70-170° C., and the reaction time is 20 min-3 h. The reaction is solvent-free or carried out in a solvent of acetic anhydride, acetic acid or mixture thereof. The molar ratio of the first quaternary ammonium slat intermediate III to N,N'-diphenylformamidine is 1:1-1:3;

More preferably the reaction temperature is 90-160° C., and the reaction time is 30 min-2 h. The reaction is solvent-free or carried out in a solvent of acetic anhydride, acetic acid or mixture thereof. The molar ratio of the first quaternary ammonium slat intermediate III to N,N'-diphenylformamidine is 1:1.2-1:3;

Most preferably the reaction temperature is 120-160° C., and the reaction time is 30 min-1.5 h. The reaction is solvent-free or carried out in a solvent of acetic anhydride. The molar ratio of the first quaternary ammonium slat intermediate III to N,N'-diphenylformamidine is 1:1.2-1:2;

Next, through a synthesizing method similar to that of III, compound of Formula V, preferably 2-methylbenzothiazole substituted by $R_1$, 2-methylbenzoxazole substituted by $R_1$, 2-methylbenzoselenazole substituted by $R_1$ or 2,3,3-trimethy-3H-indoline substituted by $R_1$, reacts with compound $R_3(CH_2)_mZ$ to obtain the second quaternary ammonium slat intermediate VI, wherein Z is halogen or OTs, and $Z^-$ is the halogen anion or $OTs^-$ generated in the reaction:

The reaction temperature is 10-180° C., and the reaction time is 4-48 h. The reaction solvent is dichloromethane, chloroform, ethanol, acetonitrile, ethyl acetate, toluene, xylene, o-dichlorobenzene or the polar organic solvents of the mixture thereof. The molar ratio of V to compound $R_3(CH_2)_mZ$ is 1:1-1:10;

Preferably the reaction temperature is 60-140° C., and the reaction time is 6-36 h. The reaction solvent is chloroform, acetonitrile, toluene, xylene, o-dichlorobenzene or the polar organic solvents of the mixture thereof. The molar ratio of V to compound $R_3(CH_2)_mZ$ is 1:1-1:6;

More preferably the reaction temperature is 80-120° C., and the reaction time is 10-24 h. The reaction solvent is acetonitrile, toluene, o-dichlorobenzene or the polar organic solvents of the mixture thereof. The molar ratio of V to compound $R_3(CH_2)_mZ$ is 1:1-1:3;

Most preferably the reaction temperature is 90-120° C., and the reaction time is 12-18 h. The reaction solvent is toluene, o-dichlorobenzene or the polar organic solvents of the mixture thereof. The molar ratio of V to compound $R_3(CH_2)_mZ$ is 1:1-1:2;

Next, react IV with the second quaternary ammonium slat intermediate VI by the catalysis of acetic anhydride with organic base (such as amine) to give the monocationic nitrogen containing compound of Formula VII:

VII

The reaction temperature is 5-130° C., and the reaction time is 10 min-6 h. The reaction is solvent-free or carried out in a solvent of dichloromethane, chloroform, methanol, ethanol, ethylene glycol monomethyl ether or the polar organic solvents of the mixture thereof. The catalyst for this reaction is a combination of acetic anhydride and organic base, the said organic base is selected from diethylamine, propylamine, triethylamine, pyridine, piperidine or mixtures thereof. The molar ratio of VI to IV is 1.5:1-1:1.5;

Preferably the reaction temperature is 20-130° C., and the reaction time is 30 min-5 h. The reaction is solvent-free or carried out in a solvent of methanol, ethanol, ethylene glycol monomethyl ether or the polar organic solvents of the mixture thereof. The said organic base is selected from triethylamine, pyridine, piperidine or mixtures thereof. The molar ratio of VI to IV is 1.2:1-1:1.5;

More preferably the reaction temperature is 30-120° C., and the reaction time is 1-4 h. The reaction is solvent-free or carried out in a solvent of methanol, ethylene glycol monomethyl ether or the polar organic solvents of the mixture thereof. The said organic base is selected from triethylamine, pyridine or mixtures thereof. The molar ratio of VI to IV is 1.2:1-1:1.2;

Most preferably the reaction temperature is 30-100° C., and the reaction time is 1.5-3 h. The reaction is solvent-free or carried out in a solvent of methanol, ethylene glycol monomethyl ether or the polar organic solvents of the mixture thereof. The said organic base is chosen from triethylamine, pyridine or mixtures thereof. The molar ratio of VI to IV is 1:1;

At last, on demand, replace the anion of compound VII with $ClO_4^-$, $PF_6^-$, $BF_4^-$ or $CH_3COO^-$ of the corresponding sodium or potassium to give the final compounds of Formula I:

I

The reaction temperature is 60-140° C., and the reaction time is 10 min-2 h. The reaction solvent is DMF, DMSO or the polar organic solvents of the mixture thereof. The molar ratio of sodium or potassium salt containing $ClO_4^-$, $PF_6^-$, $BF_4^-$ or $CH_3COO^-$ to VII is 1:1-10:1;

Preferably the reaction temperature is 70-130° C., and the reaction time is 15 min-1.5 h. The reaction solvent is DMF, DMSO or the polar organic solvents of the mixture thereof. The molar ratio of sodium or potassium salt containing $ClO_4^-$, $PF_6^-$, $BF_4^-$ or $CH_3COO^-$ to VII is 1:1-7:1;

More preferably the reaction temperature is 80-120° C., and the reaction time is 20 min-1 h. The reaction solvent is DMF. The molar ratio of sodium or potassium salt containing $ClO_4^-$, PF6, $BF_4^-$ or $CH_3COO^-$ to VII is 1:1-4:1;

Most preferably the reaction temperature is 90-110° C., and the reaction time is 30 min. The reaction solvent is DMF. The molar ratio of sodium or potassium salt containing $ClO_4^-$, $PF_6^-$, $BF_4^-$ or $CH_3COO^-$ to VII is 1:1-2:1;

The structures of the above compounds of Formula I, synthesized through the above-mentioned methods, could be confirmed through NMR spectrometry and Mass spectrometry. Their structures can also be confirmed with the $^{13}C$ NMR spectrometry and the melting point analysis in auxiliary. The most prominent structural feature of the above mentioned category of compounds with the general structural Formula I is the nitrogen containing substitute group $(CH_2)_mR_3$ introduced through the preparation of the second quaternary ammonium intermediate VI from reactant V. Wherein $^1H$ NMR chemical shift ä for the —$CH_2$— directly connected with $R_3$ in the nitrogen containing group $(CH_2)_mR_3$ is ä: 4-6 (m=1) or 2-4 (m=2~18);

In another aspect, the present invention further provides a conjugate comprising a compound of this invention and a composition comprising a compound of this invention or a conjugate thereof;

In another aspect, the present invention further provides the applications of the above mentioned compounds, conjugates and compositions thereof in biological staining.

The whole techniques chosen enable the new compounds of this invention have the following beneficial effects as fluorescent dyes:

Introduction of nitrogen containing substitute group into the molecules of the disclosed compounds increases the fluorescence quantum yield upon binding to nucleic acids and therefore the detection sensitivity is enhanced;

The nitrogen containing substitute group introduced into the molecules of the disclosed compounds is non-quaternized (non cationic) and therefore the new disclosed compounds have good live cell membrane permeability and can be utilized in a wide range of applications;

Introduction of nitrogen containing substitute group into the molecules of the disclosed compounds appropriately increases the polarity of molecules, reduces the binding with the hydrophobic structured biomolecules such as membrane lipid, protein and others and therefore displays the specific association with nucleic acids.

Compared to the benzothiazole- and indoline-based symmetric cyanine dyes having the same methine bridge, the fluorescent dyes disclosed herein, introduce a quinoline ring on one end of the molecule, and increase the maximum absorption wavelength by about 80 nm, have a fluorescence emission wavelength of 650 nm and can avoid interference from the fluorescent background of the biological samples;

The new dye compounds disclosed may be applied with a red semiconductor laser as excitation light source, which is inexpensive, small in size and stable. This greatly reduces the cost of the accompanying equipment;

The new dyes disclosed are simple in structure, readily available in raw materials, low in toxicity and side effects, cheaper than other alternatives, and can be obtained through 4-5 steps and therefore readily applied in various industries.

The features and advantages of the present invention and other features and advantages will become apparent from the following drawings and the detailed descriptions.

The compounds of the present disclosure can be used directly for staining biological samples in the form of salts as described herein. Alternatively the derivatives of the compounds of the present disclosure can also be used for staining biological samples. The said derivatives including, but not limited to, conjugates.

Typically, the conjugates are used in the fluorescence activated cell sorter (FACS). "Conjugate" as used herein refers to compounds formed by attaching the fluorescent dyes disclosed to other molecules through covalent bonds. Molecules that can be conjugated to the fluorescent dyes disclosed may be those that can bind specifically to cells or cell components, including, but not limited to, antibodies, antigens, receptors, ligands, enzymes, substrates, coenzymes, etc. Generally, the test sample is incubated with the fluorescent conjugates for a period of time so that the fluorescent conjugates bind specifically to certain cells or cell components in the test sample. The binding of the fluorescent conjugates to the cells or cell components can also be referred to as staining. The above staining step can be repeated several times in sequence, or a variety of conjugates can be used for concurrent multi-staining. After staining, analysis of the sample is conducted in the fluorescence activated cell sorter, wherein the excitation light source excites the fluorescent dyes disclosed in the conjugates and the detection apparatus detects the emitted light generated by the excited fluorescent dyes.

In another aspect, the present invention further provides a category of compositions comprising the above mentioned compounds of Formula I and the conjugates thereof, which can be used for staining biological samples.

In still another aspect, the present disclosure further provides a composition comprising the compound of above-mentioned Formula I or conjugates thereof, which is used for staining biological samples.

The composition disclosed may comprise, besides compounds of Formula I or conjugates thereof, other components required for staining biological samples, e.g., solvents, osmotic regulating agents, pH regulating agents, surfactants, etc. These components are all known in the chemistry and biochemistry industries.

The composition of the present disclosure may exist in the form of aqueous solution, or in other suitable forms that can be formulated into solution using water prior to usage.

In still another aspect, the present disclosure further provides a method for staining biological samples using the compounds of the above-mentioned Formula I or conjugates thereof, or a composition comprising the compounds of the above-mentioned Formula I. The method may include the step of contacting the compounds of the above-mentioned Formula I or conjugates thereof, or the composition comprising compounds of the above-mentioned Formula I with the biological samples. The term "contacting" as used herein may include contacting in solution or in solid phase.

To illustrate the optimization and improvement made by the disclosed compounds on dye performance, examples 7, 8, 9, 10, 11 and comparison example 15 use known compound $M_1$, new compound $M_2$ and commercially available dye EB as references. Wherein the structures of $M_1$ and $M_2$ are as follows:

EXAMPLES

Example 1

Synthesis of the Intermediate 1-ethyl-4-methylquinoline Quaternary Ammonium Salt 20 mmol of 4-methylquinoline and 40 mmol of ethyl iodide are added under argon protection into a 100 mL round-bottom flask containing 20 mL toluene, and the reaction mixture is stirred and heated to reflux for 10 h. After the mixture cools down, the precipitate is filtered and the filter cake is washed with ethyl ether and dried to give a pale-yellow solid powder in a crude yield of 85%.

Example 2

Synthesis of Compound A 10 mmol of 1-ethyl-4-methylquinoline quaternary ammonium salt and 10 mmol of N,N'-diphenylformamidine are heated while stirring in a 160° C. oil bath for 0.5 h. The resulting dark brown solid was crushed and washed several times with ethyl ether. The dry powder was crystallized from ethanol (100 mL) to give the hemidye in fair purity with a yield of 45%, into which 4.5 mmol of 1-(4-diethylamino)-butyl-2-methylbenzothiozale quaternary ammonium salt, 1.5 mL of triethylamine and acetic anhydride are added respectively, and the mixture dissolved in 25 mL ethylene glycol monomethyl ether is stirred in room temperature for 1.5 h. Then the reaction liquid is poured into ethyl ether to precipitate small, dark purple dye particles which are later filtered and dried. The dye is purified on a silica column using a gradient mixture of dichloromethane and methanol as the eluent, and the blue fraction is collected to obtain the title compound in a yield of 60%. $^1$H-NMR (400 MHz, DMSO, TMS): δ 1.20 (t, 6H), 1.23 (t, 3H), 2.05 (m, 2H), 2.18 (m, 2H), 2.55-2.65 (m, 6H), 3.74 (t, 2H), 4.55 (tetra, 2H), 6.50 (d, 1H), 7.11 (d, 1H), 7.30-8.07 (m, 8H), 8.15 (t, 1H), 8.41 (d, 1H), 8.48 (d, 1H). MS (EI) $C_{29}H_{36}IN_3S$ m/z: 458.26 $[M-I]^+$.

Example 3

Synthesis of Compound B 10 mmol of 1-(3-piperidinyl)-propyl-4-methylquinoline quaternary ammonium salt and 25 mmol of N,N'-diphenyl-formamidine in 30 mL of acetic anhydride are heated while stirring in a 120° C. oil bath for 1.5 h. After cooling, the resulting yellow solid particles is then filtered and dried. This crude product is purified on a silica column using a gradient mixture of dichloromethane and methanol as the eluent. The yellow fraction is collected with a yield of 52%, into which 5 mmol of 1-(3-piperidinyl)-propyl-2-methyl-5-methoxy-benzothiozale quaternary ammonium salt and 1.5 mL of piperidine and acetic anhydride are added respectively, and the mixture dissolved in 25 mL ethylene glycol monomethyl ether is heated to reflux while stirring in oil bath for 1.5 h. After cooling down, the reaction liquid is then poured into ethyl ether to precipitate small, green blue dye particles which are later filtered and dried. The dye is purified on an aluminium oxide column using a gradient mixture of dichloromethane and ethanol as the eluent, and the blue fraction is collected to obtain the title compound in a yield of 44%. $^1$H-NMR (400 MHz, DMSO, TMS): δ 1.22-1.26 (m, 12H), 2.34 (m, 2H), 2.38 (m, 2H), 2.62-2.74 (m, 6H), 3.73 (s, 3H), 3.78 (t, 2H), 4.58 (t, 2H), 6.50 (d, 1H), 7.11 (d, 1H), 7.30-8.07 (m, 7H), 8.15 (t, 1H), 8.42 (d, 1H), 8.48 (d, 1H). MS (EI) $C_{36}H_{47}BrN_4O_2$ m/z: 567.37 $[M-Br]^+$.

Example 4

Synthesis of Compound C 10 mmol of 1-hydroxyethyl-4-methylquinoline quaternary ammonium salt and 10 mmol of N,N'-diphenylformamidine are heated while stirring in a 160° C. oil bath for 0.5 h. The resulting dark brown solid was crushed and washed several times with ethyl ether. The dry powder was crystallized from ethanol (100 mL) to give the hemidye in fair purity with a yield of 48%, into which 5 mmol of 1-[3-(N-aminoethyl)-amino]-propyl-2-methylbenzothiozale quaternary ammonium salt, 1.5 mL of pyridine and acetic anhydride are added respectively, and the mixture dissolved in 25 mL ethylene glycol monomethyl ether is stirred in room temperature for 1.5 h. Then add the solution of 4 mmol NaClO$_4$ in 2 mL DMF into the reaction, start heating to reflux while stirring for another 30 min. After cooling down, the reaction liquid is poured into ethyl ether to precipitate small, green blue dye particles which are later filtered and dried. The dye is purified on an aluminium oxide column using a gradient mixture of dichloromethane and ethanol as the eluent, and the blue fraction is collected to obtain the title compound in a yield of 48%. $^1$H-NMR (400 MHz, DMSO, TMS): δ 2.34 (m, 2H), 2.58-2.76 (m, 6H), 3.74 (t, 2H), 3.82 (tetra, 2H), 4.65 (t, 2H), 5.15 (t, 1H), 6.50 (d, 1H), 7.12 (d, 1H), 7.30-8.07 (m, 8H), 8.15 (t, 1H), 8.41 (d, 1H), 8.48 (d, 1H). MS (EI) $C_{26}H_{31}ClN_4O_5S$ m/z: 447.22 $[M-ClO_4]^+$.

Example 5

Synthesis of Compound D 10 mmol of 1-benzyl-4-methylquinoline quaternary ammonium salt and 10 mmol of N,N'-diphenylformamidine are heated while stirring in a 160° C. oil bath for 0.5 h. The resulting dark brown solid was crushed and washed several times with ethyl ether. The dry powder was crystallized from ethanol (100 mL) to give the hemidye in fair purity with a yield of 42%, into which 4 mmol of 1-(3-anilino)-propyl-2,3,3-trimethy-5-chloro-3H-indoline quaternary ammonium salt, 1.5 mL of triethylamine and acetic anhydride are added respectively, and the mixture dissolved in 20 mL methanol is stirred in room temperature for 4 h. Then the reaction liquid is poured into ethyl ether to precipitate small, dark purple dye particles which are later filtered and dried. The dye is purified on a silica column using a gradient mixture of dichloromethane and methanol as the eluent, and the blue fraction is collected to obtain the title compound in a yield of 47%. $^1$H-NMR (400 MHz, CD$_3$OD, TMS): δ 1.73 (s, 6H), 2.34 (m, 2H), 3.08 (t, 2H), 3.74 (t, 2H), 5.71 (s, 2H), 6.48 (d, 1H), 7.12 (d, 1H), 7.21-7.80 (m, 17H), 8.15 (t, 1H), 8.41 (d, 1H), 8.48 (d, 1H). MS (EI) $C_{38}H_{37}BrClN_3$: m/z: 570.27 $[M-Br]^+$.

Example 6

Synthesis of Compound E 10 mmol of 1-chloroethyl-4,7-dimethylquinoline quaternary ammonium salt and 20 mmol of N,N'-diphenylformamidine in 30 mL of acetic anhydride are heated while stirring in a 120° C. oil bath for 1.5 h. After cooling, the resulting yellow solid particles is then filtered and dried. This crude product is purified on a silica column using a gradient mixture of dichloromethane and methanol as the eluent. The yellow fraction is collected with a yield of 47%, into which 5 mmol of 1-(N-propyl)-aminoethyl-2-methylbenzothiozale quaternary ammonium salt, 2 mL of propylamine and acetic anhydride are added respectively, and the mixture dissolved in 25 mL ethylene glycol monomethyl ether is heated to reflux while stirring in oil bath for 3 h. After cooling down, the reaction liquid is poured into ethyl ether to precipitate small, dark purple dye particles which are later filtered and dried. The dye is purified on a silica column using a gradient mixture of dichloromethane and methanol as the eluent, and the blue fraction is collected to obtain the title compound in a yield of 66%. $^1$H-NMR (400 MHz, DMSO, TMS): δ 0.96 (t, 3H), 1.23 (m, 2H), 2.35 (s, 3H), 2.55 (tetra, 2H), 2.65 (tetra, 2H), 3.74 (t, 2H), 3.86 (t, 2H), 4.65 (t, 2H), 6.50 (d, 1H), 7.11 (d, 1H), 7.30-8.07 (m, 7H), 8.15 (t, 1H), 8.41 (d, 1H), 8.48 (d, 1H). MS (EI) $C_{27}H_{31}BrClN_3Se$: m/z: 512.14 $[M-Br]^+$.

Example 7

Figure 1:
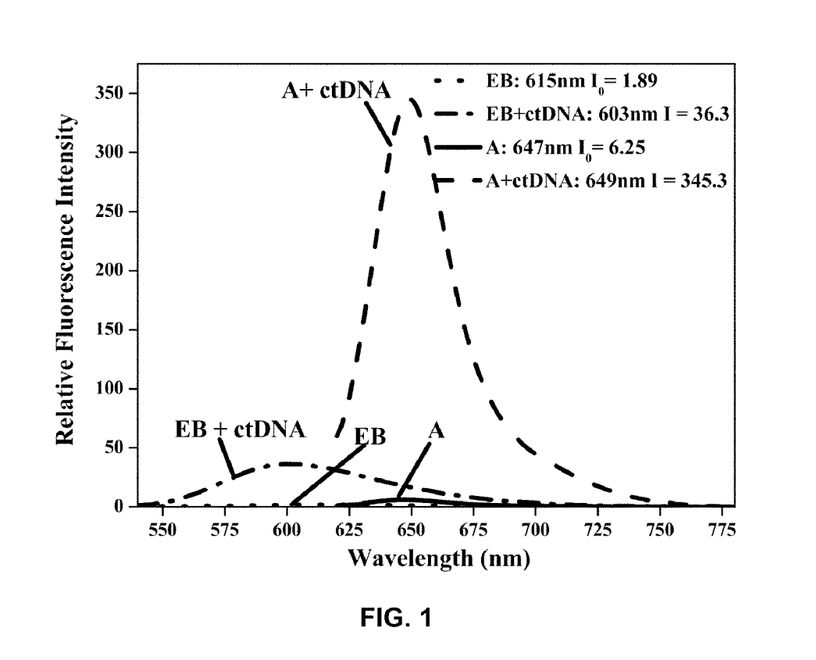
FIG. 1 is the comparison of fluorescence emission spectra of compound A with commercially available dye EB in the absence and presence of calf thymus DNA respectively in pH 7.36, 10 mM Tris-HCl buffer. The abscissa is wavelength (nm) and the ordinate is the relative fluorescence intensity. The equipments used are a UV-Vis spectrophotometer (Hp8453) and a spectrofluorophotometer (FP-6500). The concentrations of compound A, EB and calf thymus DNA are 1 μM, 1 μM and 100 μM respectively.

Determinations of the fluorescence emission spectra of compound A and commercially available dye EB in the absence and presence of calf thymus DNA respectively in buffer solution Solutions of compound A in DMSO and EB in water are separately prepared with the concentrations of 1 mM. 3 μL of each solution is diluted with 10 mM Tris-HCl buffer solution (pH 7.36) to 3 mL in a cuvette to determine its fluorescence intensity. Solution of calf thymus DNA in water is prepared, whose concentration is determined as 1.5 mM by the adsorption at 260 nm in spectrophotometry (using the molar absorption coefficients of $\epsilon_{260\,nm}$=6600 M$^{-1}$ cm$^{-1}$). Besides, another 3 μL of each solution of compound A and EB mentioned above is added into a cuvette, then 200 μL of solution of calf thymus DNA is dropped into each cuvette. Finally each mixture of dyes and calf thymus DNA solution is diluted with pH 7.36, 10 mM Tris-HCl buffer solution to 3 mL and the fluorescence emission spectra are determined respectively after stabilization. As shown in FIG. 1, under the same condition, the fluorescence of EB increases 19-fold ($I/I_0$=36.3/1.89=19) upon binding to calf thymus DNA, while the fluorescence of compound A increases 55-fold ($I/I_0$=345.3/6.25=55) upon binding to the same concentration of calf thymus DNA. The equipments used are a UV-Vis spectrophotometer (Hp8453) and a spectrofluorophotometer (FP-6500). The concentrations of compound A and EB are both 1 μM, the concentration of calf thymus DNA is 100 μM.

Example 8

Figure 2:
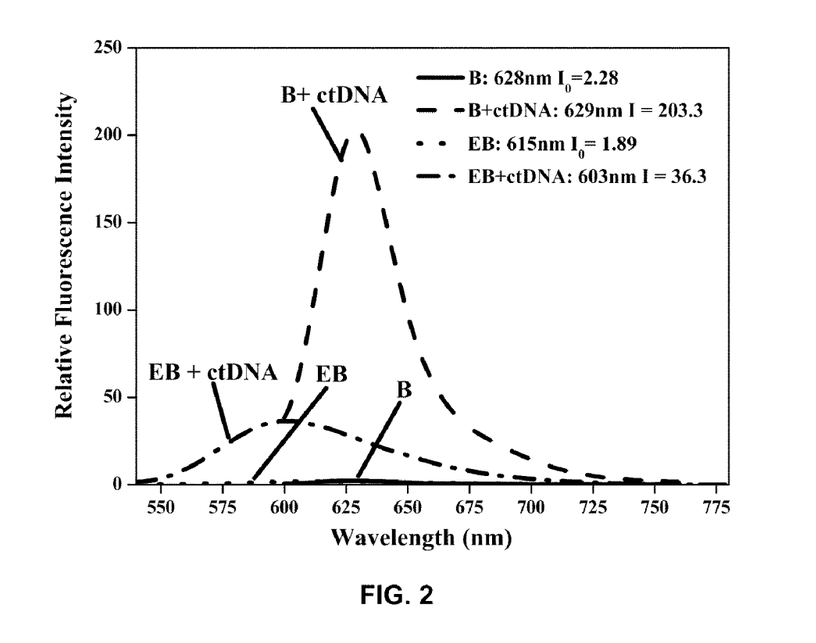
FIG. 2 is the comparison of fluorescence emission spectra of compound B with commercially available dye EB in the absence and presence of calf thymus DNA respectively in pH 7.4, 10 mM Tris-HCl buffer. The abscissa is wavelength (nm) and the ordinate is the relative fluorescence intensity. The equipments used are a UV-Vis spectrophotometer (Hp8453) and a spectrofluorophotometer (FP-6500). The concentrations of compound B, EB and calf thymus DNA are 1 μM, 1 μM and 100 μM, respectively.

Determinations of the fluorescence emission spectra of compound B and commercially available dye EB in the absence and presence of calf thymus DNA respectively in buffer solution Solutions of compound B in DMSO and EB in water are separately prepared with the concentrations of 1 mM. 3 μL of each solution is diluted with 10 mM Tris-HCl buffer solution (pH 7.4) to 3 mL in a cuvette to determine its fluorescence intensity. Solution of calf thymus DNA in water is prepared, whose concentration is determined as 1.5 mM by the adsorption at 260 nm in spectrophotometry (using the molar absorption coefficients of $\epsilon_{260\ nm}=6600\ M^{-1}\ cm^{-1}$). Besides, another 3 μL of each solution of compound B and EB mentioned above is added into a cuvette, then 200 μL of solution of calf thymus DNA is dropped into each cuvette. Finally each mixture of dyes and calf thymus DNA solution is diluted with pH 7.4, 10 mM Tris-HCl buffer solution to 3 mL and the fluorescence emission spectra are determined respectively after stabilization. As shown in FIG. 2, under the same condition, the fluorescence of EB increases fold 19-fold ($I/I_0=36.3/1.89=19$) upon binding to calf thymus DNA, while the fluorescence of compound B increases 89-fold ($I/I_0=203.3/2.28=89$) upon binding to the same concentration of calf thymus DNA. The equipments used are a UV-Vis spectrophotometer (Hp8453) and a spectrofluorophotometer (FP-6500). The concentrations of compound B and EB are both 1 μM, the concentration of calf thymus DNA is 100 μM.

Example 9

Figure 3:
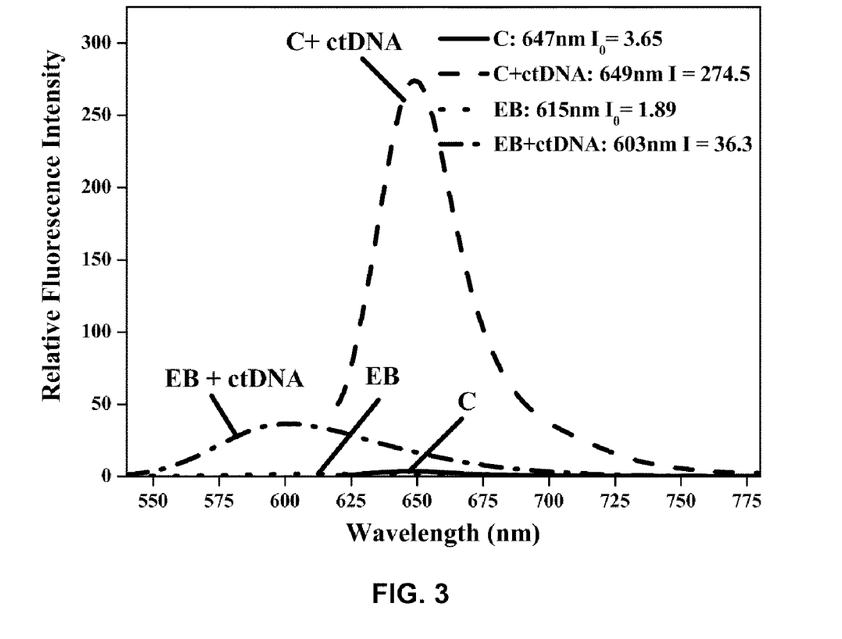
FIG. 3 is the comparison of fluorescence emission spectra of compound C with commercially available dye EB in the absence and presence of calf thymus DNA respectively in pH 7.24, 10 mM Tris-HCl buffer. The abscissa is wavelength (nm) and the ordinate is the relative fluorescence intensity. The equipments used are a UV-Vis spectrophotometer (Hp8453) and a spectrofluorophotometer (FP-6500). The concentrations of compound C, EB and calf thymus DNA are 1 μM, 1 μM and 100 μM, respectively.

Determinations of the fluorescence emission spectra of compound C and commercially available dye EB in the absence and presence of calf thymus DNA respectively in buffer solution Solutions of compound C in DMSO and EB in water are separately prepared with the concentration of 1 μM. 3 μL of each solution is diluted with 10 mM Tris-HCl buffer solution (pH 7.24) to 3 mL in a cuvette to determine its fluorescence intensity. Solution of calf thymus DNA in water is prepared, whose concentration is determined by the adsorption at 260 nm in spectrophotometry (using the molar absorption coefficients of $\epsilon_{260\ nm}=6600\ M^{-1}\ cm^{-1}$). Besides, another 3 μL of each solution of compound C and EB mentioned above is added into a cuvette, then 200 μL of solution of calf thymus DNA is dropped into each cuvette. Finally each mixture of dyes and calf thymus DNA solution is diluted with pH 7.24, 10 mM Tris-HCl buffer solution to 3 mL and the fluorescence emission spectra are determined respectively after stabilization. As shown in FIG. 3, under the same condition, the fluorescence of EB increases 19-fold ($I/I_0=36.3/1.89=19$) upon binding to calf thymus DNA, while the fluorescence of compound C increases 75-fold ($I/I_0=274.5/3.65=75$) upon binding to the same concentration of calf thymus DNA. The equipments used are a UV-Vis spectrophotometer (Hp8453) and a spectrofluorophotometer (FP-6500). The concentrations of compound C and EB are both 1 μM, the concentration of calf thymus DNA is 100 μM.

Example 10

Figure 4:
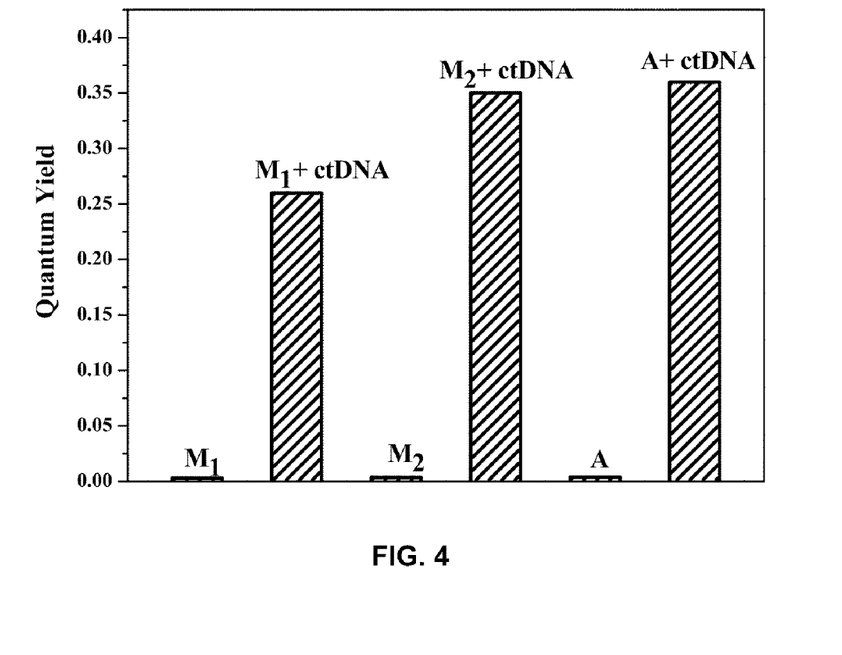
FIG. 4 is the comparison of the fluorescence quantum yields of A in the absence and presence of calf thymus DNA respectively with $M_1$ and $M_2$ in pH 7.4, 10 mM Tris-HCl buffer. The ordinate is the fluorescence quantum yield. The equipments used are a UV-Vis spectrophotometer (Hp8453) and a spectrofluorophotometer (FP-6500). The concentrations of compounds A, $M_1$ and $M_2$ are all 1 μM. The concentration of calf thymus DNA is 100 μM.
Figure 5:
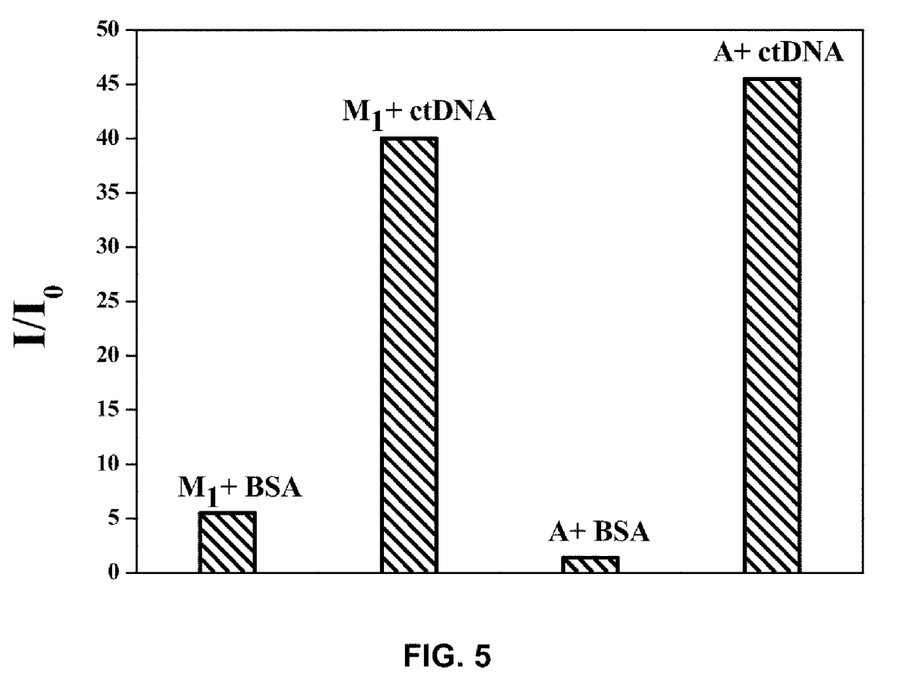
FIG. 5 is the comparison of the fluorescence increasing of A before and after the addition of bovine serum albumin and calf thymus DNA respectively in contrast with the known compound $M_1$ in pH 7.0, 10 mM Tris-HCl buffer. The ordinate is the fluorescence increasing fold. The equipment used is a spectrofluorophotometer (FP-6500). The concentrations of compounds A and $M_1$ are both 1 μM. The concentrations of calf thymus DNA and bovine serum albumin are both 40 μg/mL.

Determinations of fluorescence quantum yields of compounds A, $M_1$ and $M_2$ in the absence and presence of calf thymus DNA respectively in buffer solution Each solution of compounds A, $M_1$ and $M_2$ in pH 7.4, 10 mM Tris-HCl buffer solution, in certain concentrations, has a maximum absorbance of less than 0.1 as determined by a UV-Vis Spectrophotometer. Fluorescence intensities are measured at selected excitation wavelengths. For each compound, the determination is made in triplicate, the fluorescence quantum yield of each determination is calculated, and the mean value is taken. Using Rhodamine B as the standard ($\phi_F=0.97$, methanol, 15° C.), the calculated fluorescence quantum yields in buffer solution of compounds A, $M_1$ and $M_2$ are all less than 0.01, which illustrates that they all have low fluorescence background. Upon binding to the same concentration of calf thymus DNA (100 μM), the quantum yield $\phi_F$ is 0.26 for known compound $M_1$; the quantum yield $\phi_F$ is 0.35 for compound $M_2$; and the quantum yield $\phi_F$ is 0.36 for compound A. The monocationic cyanine compound A not only maintains the live cell membrane permeability, but also shows higher fluorescence quantum yield as shown in FIG. 4, which represents the same excellent labeling effect with the structurally similar but dicationic cyanine compounds such as compound $M_2$. The equipments used are a UV-Vis spectrophotometer (Hp8453) and a spectrofluorophotometer (FP-6500). The concentrations of compounds A and $M_1$, $M_2$ are all 1 μM, the concentration of calf thymus DNA is 100 μM.

Example 11

Determinations of the fluorescence intensities of compounds A and $M_1$ before and after the addition of bovine serum albumin and calf thymus DNA respectively in buffer solution 3 μL of each solution of compound A and $M_1$ with the same concentration of 1 mM is diluted with pH 7.0, 10 mM Tris-HCl buffer to 3 mL in a cuvette to determine the fluorescence intensity. Besides, 3 μL of each solution of compound A and $M_1$ mentioned above is added into two cuvettes, in which 4 μL of BSA (bovine serum albumin) solution with the concentration of 30 mg/mL is added later respectively. Finally each mixture of dye and BSA solution is diluted with pH 7.0, 10 mM Tris-HCl buffer solution to 3 mL and the fluorescence emission spectra are determined respectively after stabilization. In the same way, another 3 μL of each solution of compound A and $M_1$ mentioned above is added into two cuvettes, in which 200 μL of calf thymus DNA solution with the concentration of 600 μg/mL is added later respectively. Finally each mixture of dye and calf thymus DNA solution is diluted with pH 7.0, 10 mM Tris-HCl buffer solution to 3 mL and the fluorescence emission spectra are determined respectively after stabilization. Under the same condition, the fluorescence intensity of the known compound $M_1$ increases 40-fold upon binding to calf thymus DNA and 5.5-fold with the same concentration of BSA solution. While the fluorescence of compound A increases 45.5-fold upon binding with calf thymus DNA and 1.4-fold with the same concentration of BSA solution, which illustrates that compound A shows specific association with nucleic acids. The equipment used is a spectrofluorophotometer (FP-6500). The concentrations of compounds A and $M_1$ are both 1 μM, the concentrations of calf thymus DNA and bovine serum albumin are both 40 μg/ml.

Example 12

Figure 6:
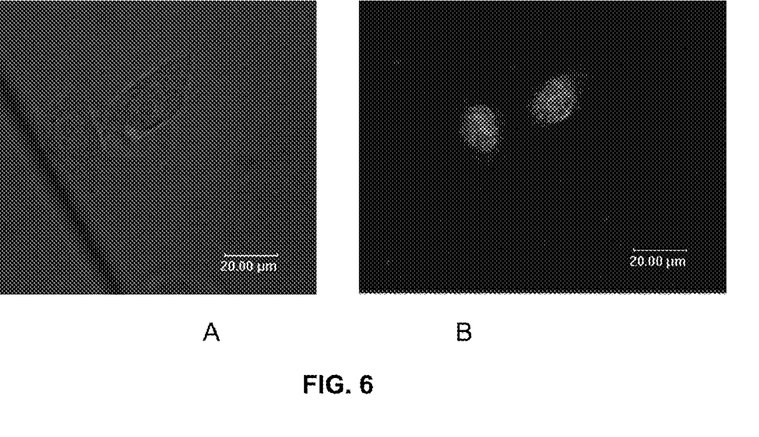

Imaging of live MCF-7 Cells Stained with Compound A by Confocal Laser Scanning Microscopy MCF-7 cells are cultured in DEME (Invitrogen) supplemented with 10% FBS (Invitrogen). One day before imaging, cells are seeded in 24-well flat-bottomed plates. The next day, the live cells were incubated with 2 μM of compound A for 30 min at 37° C. under 5% $CO_2$ and then washed with phosphate-buffered saline (PBS) three times, and then the fluorescence imaging was observed under confocal laser scanning microscopy with a 100× objective lens (excited with Cy5 channel). 1000× magnification was utilized in the imaging. The scale bar represents 20 μm. FIG. 6A is the white light image of live MCF-7 cells stained with compound A, FIG. 6B is the fluorescence image of live MCF-7 cells stained with compound A. As shown in FIG. 6B, compound A shows nucleus selective staining of live MCF-7 cells. The equipment used is a confocal laser scanning microscope (TCS-SP2). Excitation channel: Cy5 (633 nm). The concentration of compound A is 2 μM.

Example 13

Figure 7:
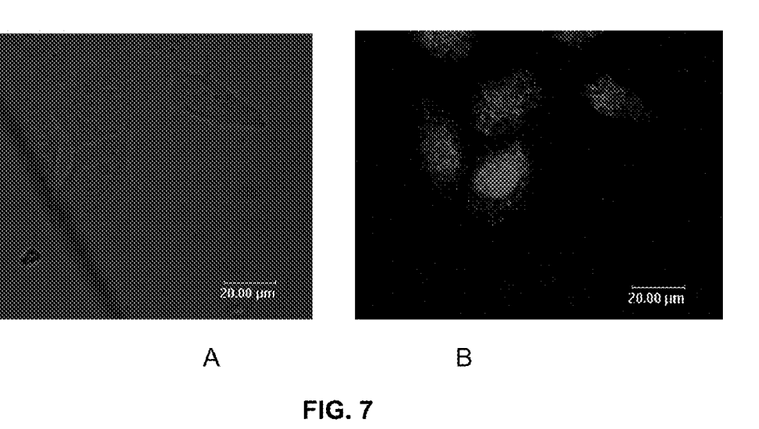

Imaging of live MCF-7 Cells Stained with Compound D by Confocal Laser Scanning Microscopy MCF-7 cells are cultured in DEME (Invitrogen) supplemented with 10% FBS (Invitrogen). One day before imaging, cells are seeded in 24-well flat-bottomed plates. The next day, the live cells were incubated with 1.5 µM of compound D for 30 min at 37° C. under 5% $CO_2$ and then washed with phosphate-buffered saline (PBS) three times, and then the fluorescence imaging was observed under confocal laser scanning microscopy with a 100× objective lens (excited with Cy5 channel). 1000× magnification was utilized in the imaging. The scale bar represents 20 µm. FIG. 7A is the white light image of live MCF-7 cells stained with compound D, FIG. 7B is the fluorescence image of live MCF-7 cells stained with compound D. As shown in FIG. 7B, compound D shows nucleus selective staining of live MCF-7 cells. The equipment used is a confocal laser scanning microscope (TCS-SP2). Excitation channel: Cy5 (633 nm). The concentration of compound D is 1.5 µM.

Example 14

Figure 8:
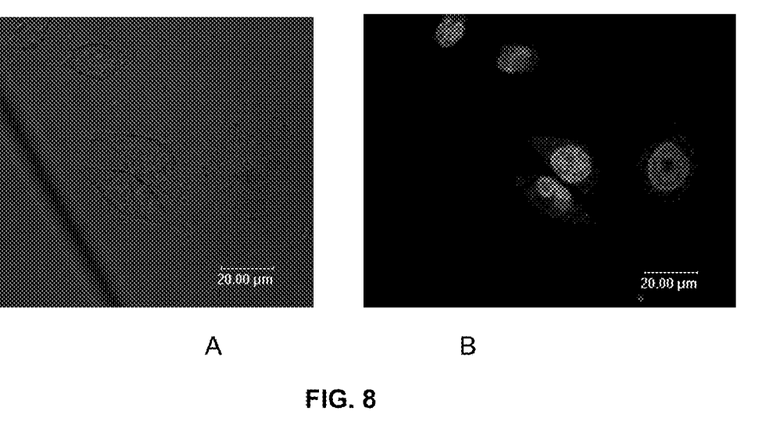

Imaging of live MCF-7 Cells Stained with Compound E by Confocal Laser Scanning Microscopy MCF-7 cells are cultured in DEME (Invitrogen) supplemented with 10% FBS (Invitrogen). One day before imaging, cells are seeded in 24-well flat-bottomed plates. The next day, the live cells were incubated with 3 µM of compound E for 30 min at 37° C. under 5% $CO_2$ and then washed with phosphate-buffered saline (PBS) three times, and then the fluorescence imaging was observed under confocal laser scanning microscopy with a 100× objective lens (excited with Cy5 channel). 1000× magnification was utilized in the imaging. The scale bar represents 20 µm. FIG. 8A is the white light image of live MCF-7 cells stained with compound E, FIG. 8B is the fluorescence image of live MCF-7 cells stained with compound E. As shown in FIG. 8B, compound E shows nucleus selective staining of live MCF-7 cells. The equipment used is a confocal laser scanning microscope (TCS-SP2). Excitation channel: Cy5 (633 nm). The concentration of compound E is 3 µM.

Comparison Example 15

Figure 9:
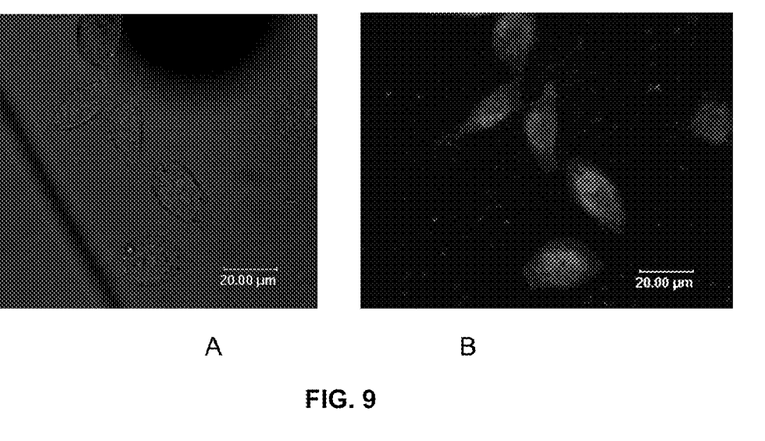

Imaging of Live MCF-7 Cells Stained with Compound $M_1$ by Confocal Laser Scanning Microscopy MCF-7 cells are cultured in DEME (Invitrogen) supplemented with 10% FBS (Invitrogen). One day before imaging, cells are seeded in 24-well flat-bottomed plates. The next day, the live cells were incubated with 2 µM of compound $M_1$ for 30 min at 37° C. under 5% $CO_2$ and then washed with phosphate-buffered saline (PBS) three times, and then the fluorescence imaging was observed under confocal laser scanning microscopy with a 100× objective lens (excited with Cy5 channel). 1000× magnification was utilized in the imaging. The scale bar represents 20 µm. FIG. 9A is the white light image of live MCF-7 cells stained with compound $M_1$, FIG. 9B is the fluorescence image of live MCF-7 cells stained with compound $M_1$. As shown in FIG. 9B, compound $M_1$ shows simultaneously nucleus and cytoplasm staining of live MCF-7 cells, which means non-specific staining. The equipment used is a confocal laser scanning microscope (TCS-SP2). Excitation channel: Cy5 (633 nm). The concentration of compound $M_1$ is 2 µM.

The contents above are further details of the present invention with preferred specific implementations. We can not identify these specific implementations are limited to these instructions. As for the general technical staff of the technology field this invention relates to, under the premise of not departing from the conceptions of this invention, a number of simple deductions or replacement can also be made, which should be regarded as belonging to the protection scope of the present disclosure. Application as fluorescent dyes is one but never the single use of the new compounds disclosed here. As for the common technical staff of the technology area this invention relates to, based on the same mechanism as compounds of this invention used for fluorescent dyes, several simple deductions to other applications should be regarded as belonging to the protection scope of the present invention.

What is claimed is:

1. A category of fluorescent dyes, having Formula I:

wherein X is $C(CH_3)_2$, O, S, or Se, m is an integer from 1 to 18, $R_1$ and $R_2$ are each independently selected from the group consisting of H, $C_{1-18}$alkyl, $OR_7$, $C_{1-6}$alkyl-$OR_7$ and halogen, $R_3$ is selected from the group consisting of pyrrolyl, imidazolyl, piperidinyl, piperazinyl, morpholinyl, guanidino, $NHR_5$ and $N(R_6)_2$, $R_4$ is selected from the group consisting of $C_{1-18}$alkyl, benzyl and $(CH_2)_m R_3$; said benzyl is optionally substituted with one or more substituents, independently selected from the group consisting of H, $C_{1-18}$alkyl, CN, COON, $NH_2$, $NO_2$, OH, SH, $C_{1-6}$alkoxy, $C_{1-6}$alkyl amino, $C_{1-6}$amido, halogen and $C_{1-6}$ halo-alkyl, $R_5$ is selected from the group consisting of saturated and/or unsaturated, straight-chained and/or branched-chained $C_{1-18}$alkyl, hydroxy alkyl, mercapto-alkyl, amino alkyl, and acyl, $R_6$ is a $C_{2-18}$alkyl, $R_7$ is H or a $C_{1-18}$alkyl, and $Y^-$ is an anion.

2. The fluorescent dyes according to claim 1, wherein $R_1$ and $R_2$ are each independently selected from the group consisting of H and $C_{1-18}$alkyl.

3. The fluorescent dyes according to claim 1, wherein $R_3$ is selected from the group consisting of $NHR_5$, $N(R_6)_2$, pyrrolyl and piperidinyl.

4. The fluorescent dyes according to claim 1, wherein $R_4$ is selected from the group consisting of $C_{1-18}$alkyl and benzyl.

5. The fluorescent dyes according to claim 1, wherein $Y^-$ is selected from the group consisting of halogen anion, $ClO_4^-$, $PF_6^-$, $BF_4^-$, $CH_3COO^-$ and $OTs^-$.

6. The fluorescent dyes according to claim 1, selected from the group consisting of:

and

7. A conjugate including a fluorescent dye according to claim 1.

8. The synthesizing method of the fluorescent dyes according to claim 1, comprising:

1) reacting 4-methyl-quinoline heterocyclic aromatic compound II with compound R$_4$Z to obtain the first quaternary ammonium slat intermediate III, wherein Z is halogen or OTs and Z$^-$ is the reaction generated halogen anion or OTs$^-$:

wherein a reaction temperature is 10-180° C., a reaction time is 4-48 h, a reaction solvent is dichloromethane, chloroform, ethanol, acetonitrile, ethyl acetate, toluene, xylene o-dichlorobenzene or mixtures thereof, and a molar ratio of II to compound R$_4$Z is 1:1-1:10;

2) condensing the first quaternary ammonium slat intermediate III from 1) with N,N'-diphenylformamidine to get the compound of Formula IV:

wherein a reaction temperature is 50-200° C., and a reaction time is 15 min-4 h, and the reaction is solvent-free or carried out in a solvent of acetic anhydride, acetic acid or mixtures thereof, and a molar ratio of the first quaternary ammonium slat intermediate III to N,N'-diphenylformamidine is 1:1-1:4;

3) reacting compound V with compound R$_3$(CH$_2$)$_m$Z to obtain the second quaternary ammonium slat intermediate VI, wherein Z is halogen or OTs and Z$^-$ is the reaction generated halogen anion or OTs$^-$:

VI wherein a reaction temperature is 10-180° C., and a reaction time is 4-48 h, a reaction solvent is dichloromethane, chloroform, ethanol, acetonitrile, ethyl acetate, toluene, xylene, o-dichlorobenzene or mixtures thereof, and a molar ratio of V to compound $R_3(CH_2)_mZ$ is 1:1-1:10;

4) reacting the second quaternary ammonium slat intermediate VI from 3) with IV to give the compound of Formula VII:

VII wherein a reaction temperature is 5-130° C., and a reaction time is 10 min-6 h, a reaction is solvent-free or carried out in a solvent of dichloromethane, chloroform, methanol, ethanol, ethylene glycol monomethyl ether or mixtures thereof The catalyst for this reaction is a combination of acetic anhydride and organic base, and a molar ratio of VI to IV is 1.5:1-1:1.5, wherein X, m, $R_1$, $R_2$, $R_3$, $R_4$, $R_5$, $R_6$ and $R_7$ are defined according to claim 1, 5) replacing the anion of compound VII with $Y^-$ of the corresponding sodium or potassium to give the final compound of Formula I:

I wherein a reaction temperature is 60-140° C., and a reaction time is 10 min-2 h, a reaction solvent is DMF, DMSO or mixtures thereof, and a molar ratio of sodium or potassium containing $Y^-$ to VII is 1:1-10:1, wherein $Y^-$ is defined according to claim 1.

9. A biological stain composition comprising a fluorescent dye according to claim 1.

10. A method for biological stain, comprising bringing a biological sample into contact with a fluorescent dye according to claim 1.

11. A biological stain composition comprising a fluorescent dye according to claim 7.

12. A method for biological stain, comprising bringing a biological sample into contact with a fluorescent dye according to claim 7.

13. A method for biological stain, comprising bringing a biological sample into contact with a biological stain composition according to claim 9.

* * * * *